United States Patent [19]

Shapiro

[11] 4,423,931

[45] Jan. 3, 1984

[54] FUNDUS CAMERA ACCESSORY FOR ANALYSIS OF THE OCULAR FUNDUS CONTOUR

[76] Inventor: Jerrold M. Shapiro, 34 Parker Rd., Framingham, Mass. 01701

[21] Appl. No.: 185,585

[22] Filed: Sep. 9, 1980

[51] Int. Cl.³ .............................................. A61B 3/10
[52] U.S. Cl. .................................... 351/206; 351/211; 354/62; 356/376
[58] Field of Search ................... 351/6, 7, 13, 14, 206, 351/211, 220, 221; 354/62; 356/376

[56] References Cited

U.S. PATENT DOCUMENTS

| 2,049,223 | 7/1936 | Reason | 351/13 |
| 3,424,518 | 1/1969 | Sato et al. | 351/13 |
| 3,614,237 | 10/1971 | Kyle | 356/376 |
| 3,943,278 | 3/1976 | Ramsey | 356/376 |

FOREIGN PATENT DOCUMENTS 840169 8/1951 Fed. Rep. of Germany .......... 351/6

Primary Examiner—R. A. Rosenberger
Attorney, Agent, or Firm—Hamilton, Brook, Smith & Reynolds

[57] ABSTRACT

An accessory is provided to enable the use of a fundus camera in the photogrammetric analysis of the ocular fundus contour. The accessory includes a stripe projector which projects an image of a grating such that the grating appears to be at infinity. This is accomplished by placing the grating at about the rear focal plane of the projection lens system. A mirror reflects the projected stripes into the eye along a projection axis parallel to the camera optic axis. The mirror also serves as an aperture stop near the eye so that the grating is clearly imaged at all depths of the optic disc cup. A predetermined relationship between the projection optic axis and fundus camera optic axis is maintained by supporting the projector from the front lens housing of the fundus camera. To that end, a sleeve fixed to the projector fits closely around the lens housing. The light source may be one of coherent or incoherent light.

17 Claims, 10 Drawing Figures

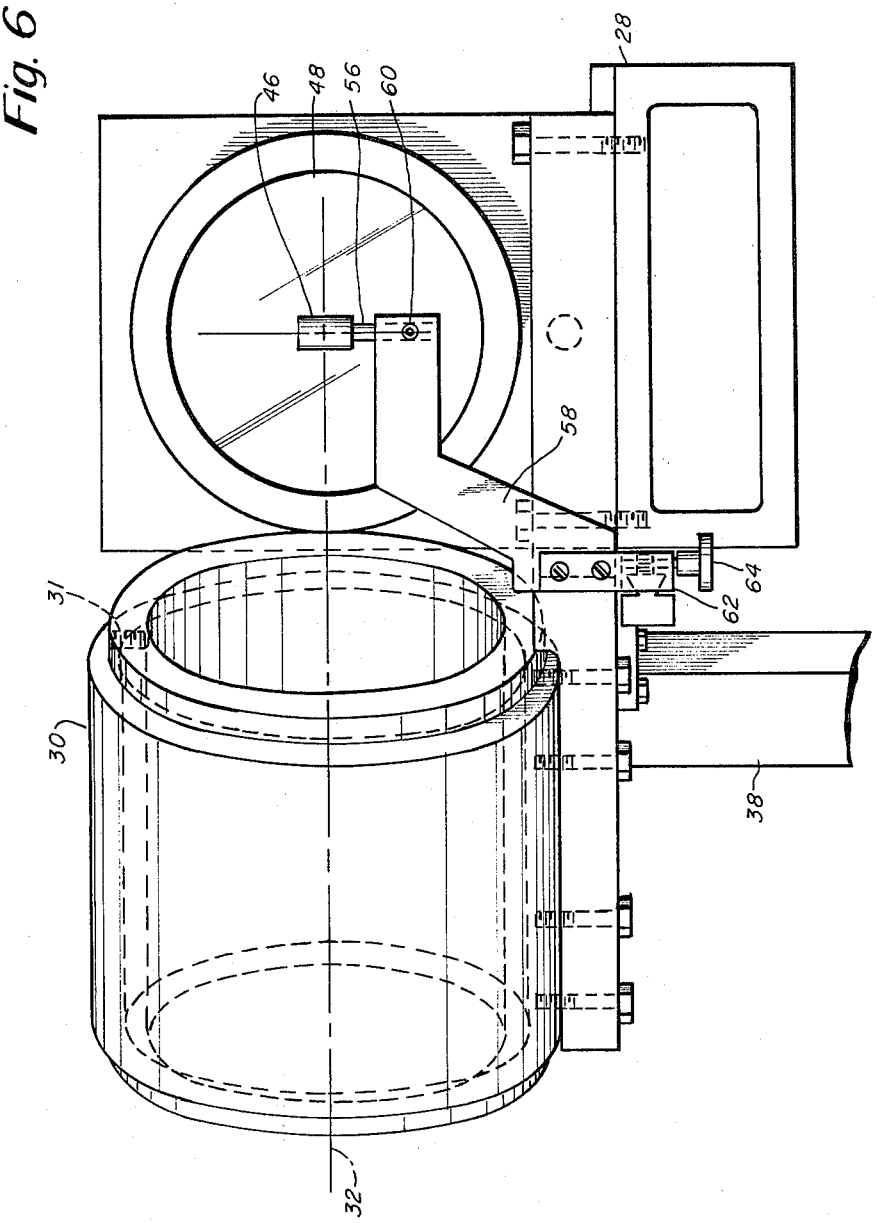

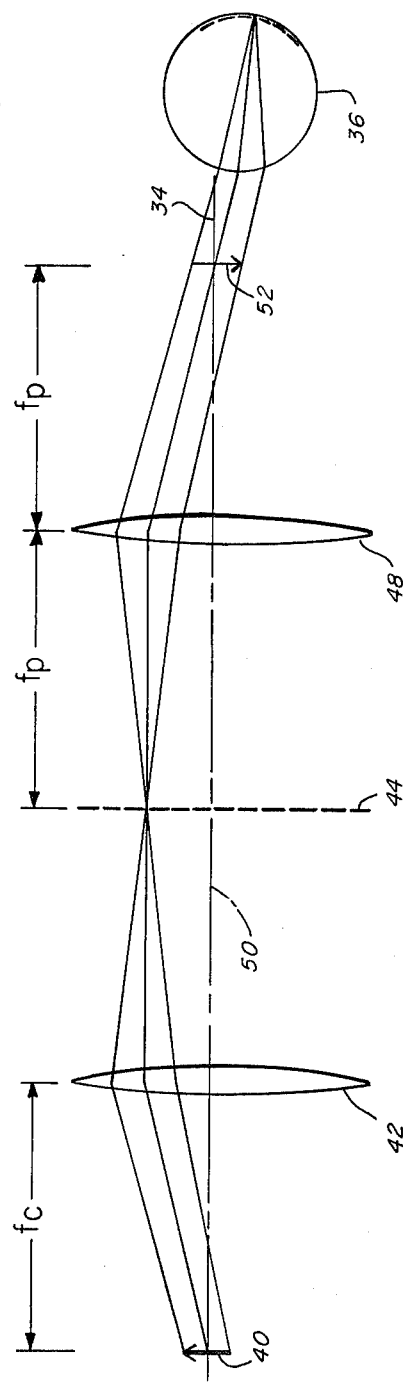

FUNDUS CAMERA ACCESSORY FOR ANALYSIS OF THE OCULAR FUNDUS CONTOUR

GOVERNMENT SPONSORSHIP

Work relating to this invention was partially supported by Grant No. 1 RO1 EY 01788-05 from the National Institute of Health.

DESCRIPTION

Technical Field

This invention relates to the analysis of the ocular fundus contour and, in particular, to a system for projecting stripes onto the fundus.

Background

The shape of the normal eye is maintained by an internal fluid pressure of about 15 mm of mercury. That intraocular pressure (IOP) is controlled by the balance of flow of aqueous humor due to secretion from the ciliary body and drainage through the trabecular meshwork. In the disease of glaucoma, the balance is disturbed.

The most widely used test for glaucoma has been a measurement of the IOP. Although elevated intraocular pressure is useful in screening large populations for glaucoma, IOP alone is not reliable for making decisions about when and how to treat the individual patient. There are wide variations in the susceptibility of a given eye to a given pressure. An IOP which is well above the average of the population may be well tolerated by some patients, while an average IOP may be intolerable in other patients. Furthermore, the elevation of IOP in a prospective glaucoma patient may precede, by many years, other changes in the eye. If patients were treated based upon IOP alone, then many patients who would never progress to visual loss would be treated needlessly, while those who are destined for visual loss in fifteen years would be treated needlessly for up to seven years. For this reason, it is common practice to examine the patient for evidence of visual loss.

The visual field examination is designed to locate regions of the retina with lower than normal light sensitivity. In glaucoma, these regions occur in characteristic patterns over the retina. Unfortunately, the visual field examination is highly subjective, and its results depend upon many factors in addition to retinal sensitivity such as mental alertness of the patient, patient anxiety, and skill of the examiner. When glaucoma is first detected on a visual field examination, progressive changes may have already begun to "snowball", and treatment may not be able to prevent blindness. For this reason, the attention of the clinical and research communities is focused on the region of the eye where the nerve fibers of the retina exit to the brain: the optic nerve head or optic disc.

Changes in blood circulation and in the transport of cell components within the nerve fibers have been found in the optic disc during elevation of IOP. Optic nerve head tissue gradually dies, and a "caving in" or excavation of the optic disc deepens and gets wider as glaucoma damages the nerves. These changes in the topography of the optic disc surface are believed to precede visual field loss in many cases. In addition, the topographic changes can be measured objectively, whereas the visual field examination is highly subjective. A change in optic disc topography is objective evidence that the prevailing IOP is too high for that eye.

Because the normal magnitude of the optic disc depression varies from patient to patient, one must observe changes in the depression over a lengthy period of time to detect glaucoma. It is estimated that the depressions in eyes subject to glaucoma increase at about eighteen percent per year. A specification of six percent as an upper limit for the measurement error will ensure that the probability of mistakenly diagnosing an eighteen percent change when there is actually no change is less than two percent. This error is medically acceptable.

Small measurement errors are difficult to achieve. The optic disc is only 1.5 mm in diameter, and its cup is usually less than 0.5 mm wide and less than 0.3 mm deep. The optic disc is not readily accessible, and its surface is not well defined. The glial and nerve tissues of the optic disc are translucent, and are diffuse scatterers of light. Aside from the blood vessels emerging from its center, the optic disc surface is devoid of features. It is therefore difficult to use conventional topographic methods, such as stereophotogrammetry, to map the optic disc surface. Although stereophotogrammetry of the optic disc has the potential for high precision, the potential is only reached at considerable expense due to the need for sophisticated equipment.

In the slitlamp method for assessing the optic disc, the simple uniform illumination used in stereophotography is exchanged for a more complicated illumination in order to more simply extract the depth information from the resulting image.

The slitlamp was introduced by Gullstrand in 1911 and has become an essential tool in the examination of both the anterior segment and the fundus of the eye. The underlying principle is optic sectioning. Light is projected through a slit, and the slit is imaged into the eye. The resultant narrow stripe of light intersecting the surface and viewed at an angle allows an observer to see the surface contours in section. The slitlamp is used in conjunction with a camera for recording the contour. But the single stripe reveals the topography in only one small region, and therefore the stripe must be scanned over the surface to give a total picture. The difficulty of making a mosaic of the photographs of the single stripe and the alignment errors in such a process preclude the use of a scanned stripe for quantitating the topography. This difficulty was overcome by replacing the single slit with a photographic mask that contains several slits in a grating. (Holm and Krakau 1965).

The multiple slit method was originally developed for measuring the volume of superficial tumors and of swelling of the gums in periodontal diseases. The original equipment included one or two cameras and a slit projector, mounted so that their optical axes were in the same plane and met in a common point centered on the object under study. In order to apply the multiple slit method to the interior of the eye, two modifications to the equipment has to be made. First, the optical power of the eye was neutralized by the application of a contact lens so that the retina appeared to the apparatus to be located a short distance behind the eye's pupil. Second, the angle between the axes of the camera and slit projector was reduced from thirty to fifteen degrees so that light rays from the eye to the apparatus would pass through the small opening of the pupil.

The principle behind the extraction of topographic data from slit photographs is a modified form of the parallactic displacement principle which underlies stereophotogrammetry. In stereophotogrammetry, depth information is obtained by first overlaying, in practice or in principle, the two stereophotographs so that features such as blood vessel branchings on the retinal surface are aligned, and by then measuring the horizontal displacement between the two images of features on the optic disc surface. If stereophotographs were taken of the projected slits from a slitlamp in such a way that the first camera was in its usual position, and the second camera axis was aligned with the axis of the slit projector, then a stereo pair would be obtained in which the first camera's picture would be the usual slit photograph, while the other picture would be a set of straight lines. This is due to the fact that the second camera views each planar slit on edge. Since, in the slit photograph, the features used for alignment are the slits that are projected onto the surface, depth information could be obtained by overlaying the two pictures so that the portions of the slits that are on the retinal surface are aligned, and by then measuring the horizontal displacement between the two images of each slit on the optic disc surface. Since the second picture is known to consist of straight lines, it is not actually recorded; instead, a set of straight lines is drawn on the first photograph so as to connect the retinal portions of each slit and establish a reference base plane. Since the second picture is known in advance, slit photography is a special form of simultaneous stereophotography. As such, depth errors due to errors in the stereo base are minimal, since the slit projector and camera are rigidly mounted to each other. The primary source of error is the inability to precisely locate the line of intersection of each slit with the optic disc surface due to blurring.

Like stereophotogrammetry, multiple slit methods are dependent for their precision on detail in the fundus image. Since the details in a slit image are the slits themselves, the highest precision is expected when the number of slits per unit distance on the surface, the slit spatial frequency, is at a maximum. Optical resolution limitations of the eye and of the slit projector cause the stripes on the retina to become more blurred as their spatial frequency increases. Optical depth of field limitations cause the slits which are focused on the retina to go out of focus as they traverse the deeper parts of the optic cup. With conventional optical systems, any attempt to increase the maximum slit spatial frequency results in a disproportionate reduction in the depth of field. To obtain sharp stripes from the retina into the optic disc depression, an optical depth of field of about 1.1 mm is required.

The optical limitations of the conventional slit projector were overcome by forming the slits of light by an entirely different principle. A single beam of light from a laser is split into several beams, two of which are then recombined at a slight angle to produce an interference pattern of bright and dark stripes. Since the bright stripes are produced by constructive interference, they appear wherever the two beams overlap, and are therefore in focus over a great depth. If only two beams are used to form the interference pattern, then the depth of field of the projected stripes is independent of their spatial frequency, and the maximum spatial frequency which can be used is optically limited only by the camera which photographs the stripes.

To eliminate a speckle pattern which accompanies coherent illumination and to minimize the effects of scattered light at the fundus, fluorescein angiography has been used in conjunction with the coherent light method. A fluorescent dye injected into the blood stream enhances the stripe image on the fundus. This technique is known as laser contour angiography.

Although laser contour angiography has proved a reliable technique, it suffers from the need for a large and expensive laser. It is thus not suited for use in most clinics. An object of this invention is to provide a system for accurately obtaining ocular fundus contour information without the need for laser illumination.

Fundus cameras are used to photograph the ocular fundus without the need for a contact lens on the eye and are found in many clinics. A further object of this invention is to provide a stripe projection accessory to fundus cameras which readily adapts those cameras to fundus contour photogrammetry but which can be removed from the cameras so as not to interfere with other uses of the cameras.

A stripe projection system meeting the object of this invention must provide high resolution stripes on the optic fundus with a depth of field of about 1.0 mm or greater.

DISCLOSURE OF THE INVENTION

In a photogrammetry system for obtaining ocular fundus contour information, light stripes are imaged onto the retina and optic disc of a patient's eye and the stripes are photographed by a fundus camera. The camera views the stripes off-axis from the stripe projection system. In the stripe projector, a grating is positioned at about the rear focal plane of a projection lens system. Light from each point on the grating is focused onto the retina and optic disc by the eye. To provide for a large depth of field, an aperture stop is close to, or is imaged close to, the pupil of the eye.

Preferably, the stripe projector is an acessory which may be easily mounted to or removed from a fundus camera. In the preferred system, a small mirror serves as the aperture stop and is positioned within a few millimeters of the eye. Proper positioning of the optical rail which supports the projector relative to the fundus camera is assured by a rail supporting sleeve which fits closely about the front lens housing of the fundus camera.

BRIEF DESCRIPTION OF THE DRAWINGS

The foregoing and other objects, features and advantages of the invention will be apparent from the following more particular description of illustrative embodiments of the invention, as illustrated in the accompanying drawings in which like reference characters refer to the same parts throughout the different views. The drawings are not necessarily to scale, emphasis instead being being placed upon illustrating the principles of the invention.

FIG. 6 is an end view of the accessory;

FIG. 7 is an optical schematic illustrating principles of the invention;

PREFERRED MODE OF THE INVENTION

Figure 1:
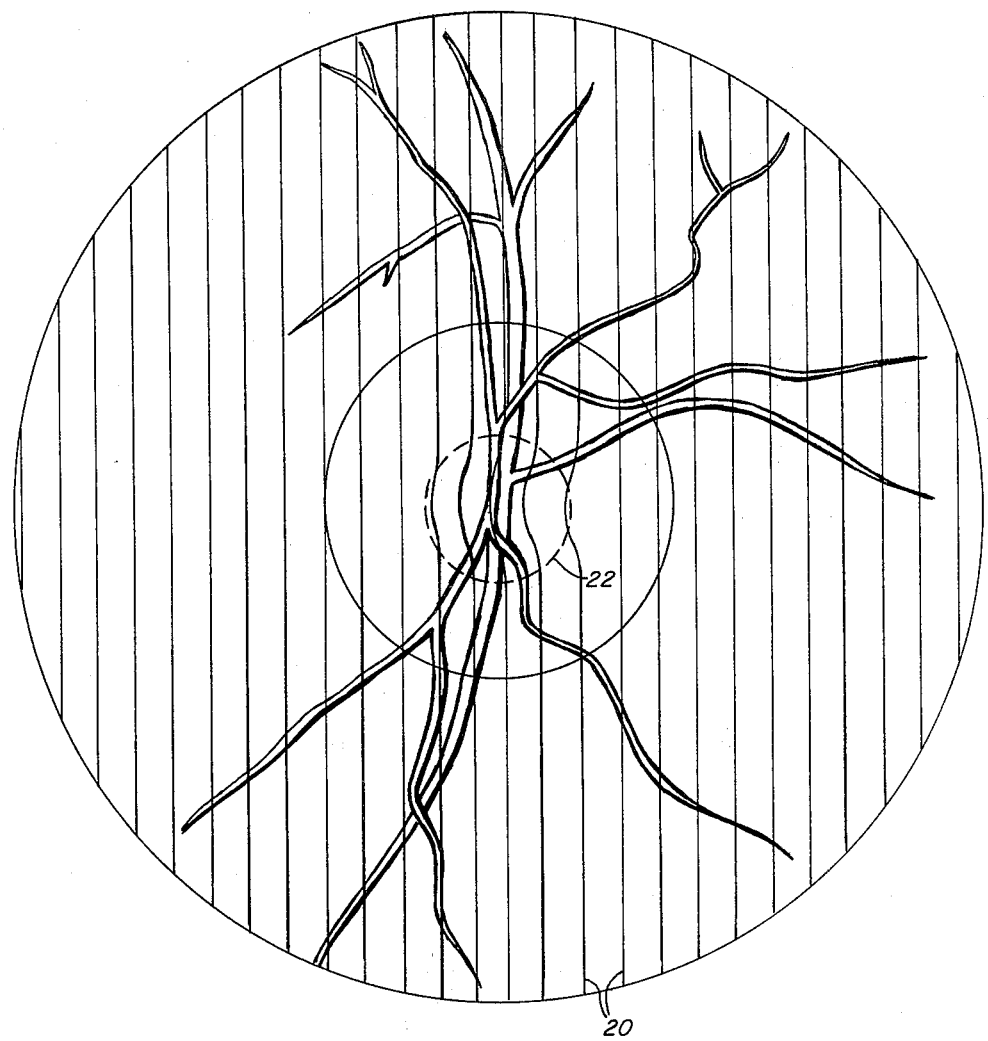
FIG. 1 is an illustration of an ocular fundus image having stripes imaged thereon and recorded by means of a fundus camera.

FIG. 1 illustrates a negative photographic exposure of an ocular fundus. Retinal arteries and veins can be seen. To provide contour information of the fundus a number of stripes 20 were projected onto the fundus by a system to be described. The camera views the stripes 20 off-axis from their projection axis. Thus, any contour in the fundus can be seen as bends in the stripes. These stripes can be seen as foreshortened cross sections of the fundus. They can be analyzed to provide depth and volume information about the cup in the optic disc 22. Computer analysis of the contour information provided by the photograph can be made by the procedures outlined in my doctoral dissertation, "Laser Contour Angiography: A New Technique forQuantifying the Topography of the Optic Disc of the Eye," which is available from Xerox-University Microfilms, Ann Arbor, Michigan Data defining the bends in the stripes can be extracted from the photograph as described in "Early Diagnosis of Glaucoma: A Microprocessor-based System," J. M. Shapiro, M. M. Kini, D. E. Philpott, Proceedings of the 31st Annual Conference on Engineering in Medicine and Biology, Vol. 20, p. 161, 1978.

Figure 2:
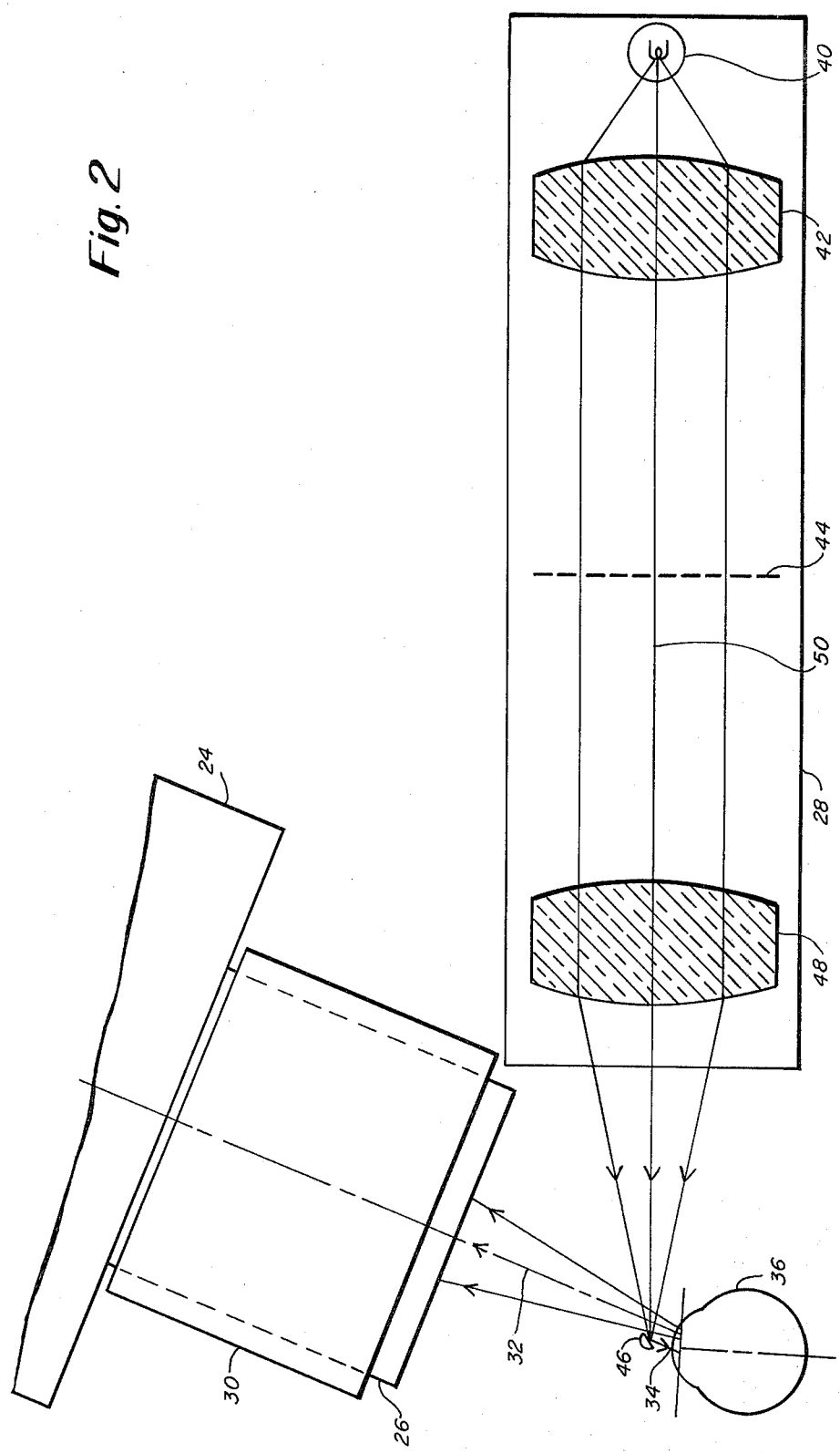
FIG. 2 is a top view, partially in schematic form, of a stripe projector embodying this invention mounted to a fundus camera.
Figure 3:
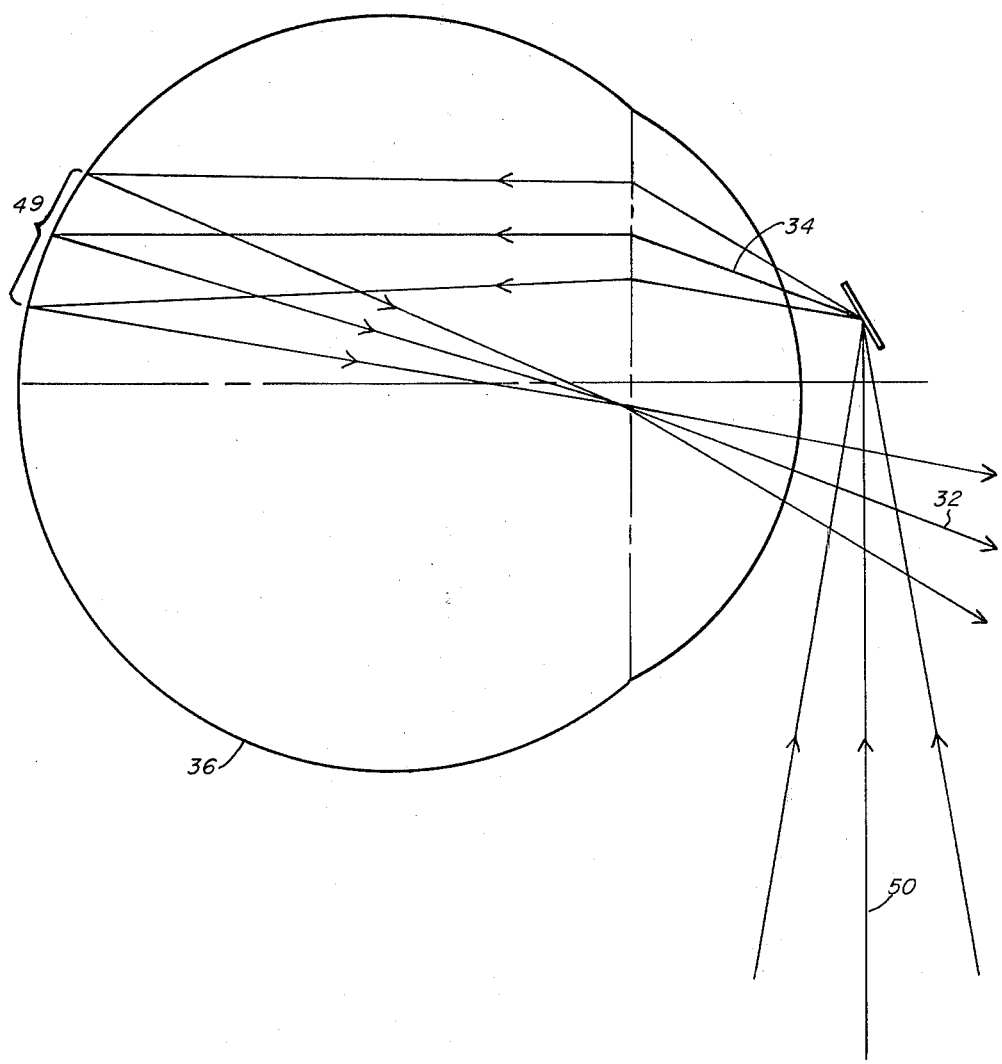
FIG. 3 is a portion of the view of FIG. 2 enlarged.
Figure 4:
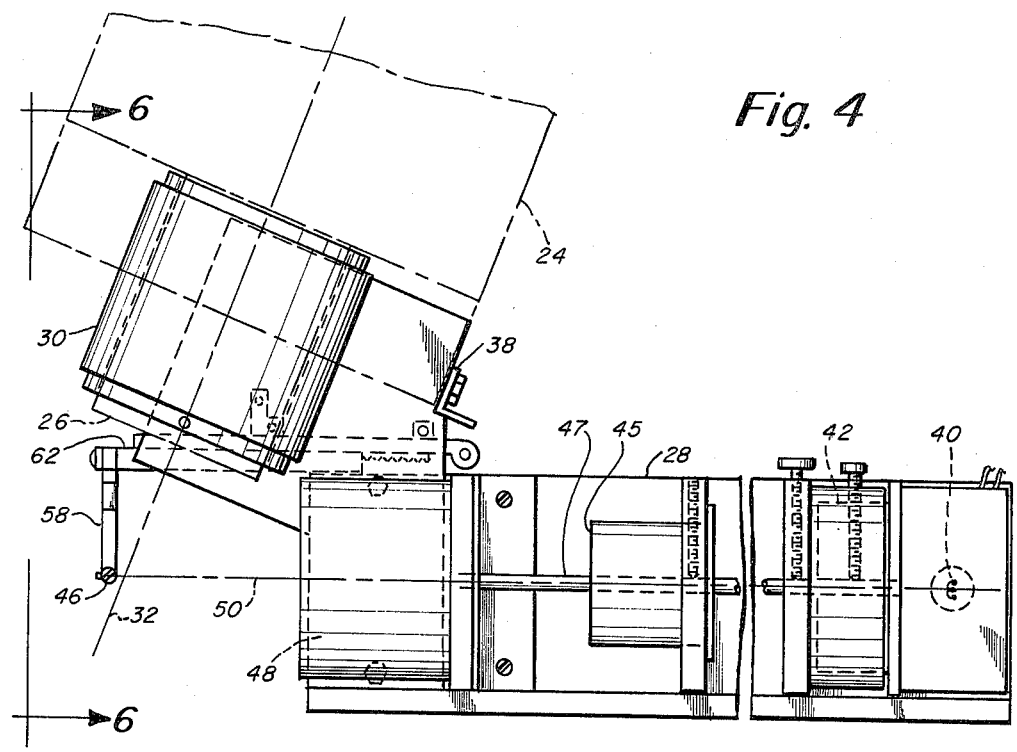
FIG. 4 is a more detailed top view of the projector accessory of FIG. 2.
Figure 5:
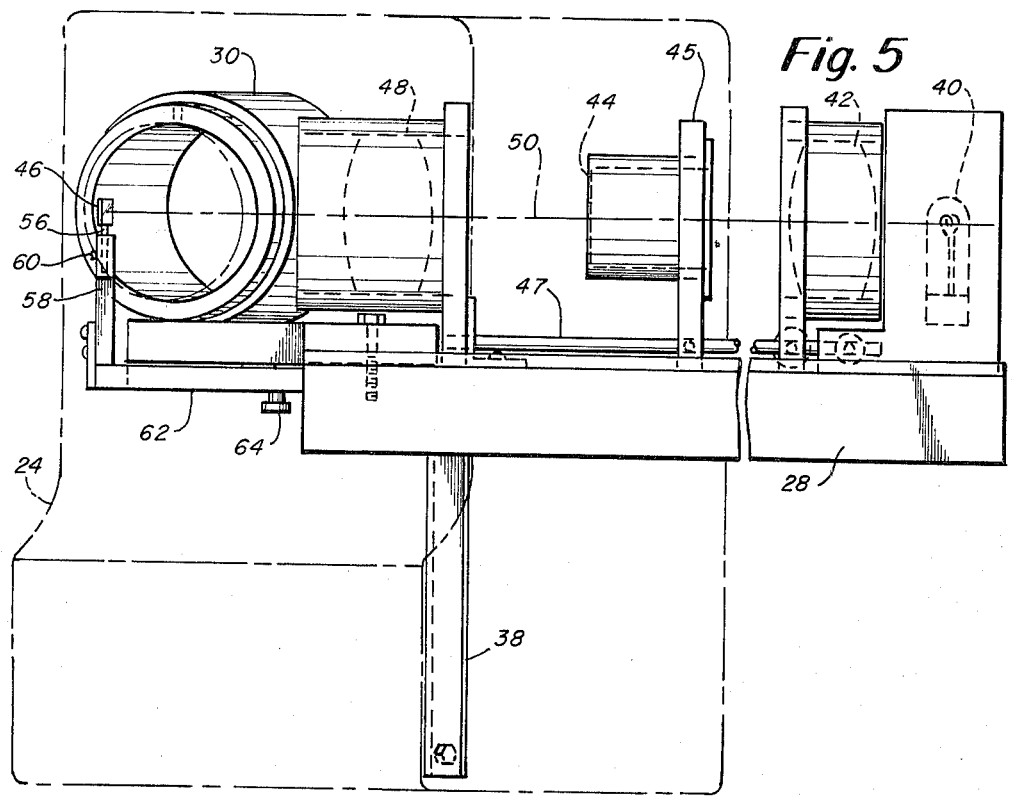
FIG. 5 is a side view of the projector accessory.

A partial schematic of a stripe projector associated with a fundus camera is shown in FIG. 2. The portion of the schematic including a mirror and the eye is enlarged in FIG. 3. FIGS. 4, 5 and 6 are more detailed views of the projector accessory. A conventional fundus camera 24 has a front lens housing 26. The conventional system also includes a chin cup and forehead rest, not shown, to stabilize the patient's head. Mechanical movements in the system allow for proper positioning of the camera relative to the patient's eye. An optical rail 28 which supports the stripe projector system is itself supported on the lens housing 26 by means of a closely fitting sleeve 30. The sleeve is fixed to the lens housing by a set screw 31. The angle of the sleeve relative to the rail assures that the optic axis 32 of the fundus camera is parallel to but offset from the optic axis 34 of the stripe projector as seen by the eye 36 of the patient. Rotation of the optical rail 28 about the fundus camera axis 32 is prevented by means of an arm 38 which is angled downward from the optical rail and is pressed against the camera by the weight of the rail. The projector accessory can be adapted for use with any fundus camera by providing a sleeve which is suitable for the particular lens housing.

Because the stripe projector is supported entirely by the lens housing of the fundus camera, it is preferably of light weight material. Although the projector will be described in terms of lens systems of single lens elements 42 and 48, these lenses should be of photographic quality and are thus actually multiple element lens systems.

The stripe projector includes a light source 40, the light from which is collimated by a collimating lens 42. The light from lens system 42 illuminates a grating 44, the image of which is to be projected onto the ocular fundus of the eye 36. The grating is a photographic negative having transparent stripes of 100 microns width, spaced by opaque regions which are 900 microns wide. The grating is held in an assembly 45 which may be moved along a rod 47 for focusing of the grating image onto the fundus.

The collimated light from the light source 40 which passes through the grating 44 is focused by a projection lens system 48 onto the front focal plane of that lens system. A small mirror 46 is located in that focal plane. The light is reflected from the mirror 46 through the dilated pupil of the eye 36 and is imaged by the eye onto the fundus at 49. The resultant image viewed by the camera is as shown in FIG. 1. That image is viewed by the camera 24 along a camera axis 32 which is offset from the projector optic axis 34 so that the stripes are seen to bend into the contour of the fundus.

The optic axis 50 of the stripe projector leading into the mirror 46 forms an acute angle of about 75 degrees with the camera axis. This assures that the beam from the projector will not be shadowed by either the lens assembly 26 of the fundus camera or by the cheek of the patient.

In slitlamp systems, discussed above, the patient is required to wear a contact lens to negate the optical power of the eye itself. Slitlamps are thus not suited for use with fundus cameras which view the fundus of a naked eye. The present system projects a clear stripe image onto the fundus without the need for a contact lens to negate the optical power of the eye. This is done by imaging the grating onto the eye in such a way that it appears to be from an infinite source. The muscles which control the ocular lens curvature are paralyzed by cycloplegic eye drops during the procedure; if emmetropic, the eye forms on the retina an image of an object at infinity. The optical system provides that the rays from any point on the grating approach the eye approximately in parallel so that they appear to come from a source at infinity. This is accomplished by positioning the grating at the rear focal plane of the projection lens system. If the eye is ametropic, the location of the grating along the projector optic axis must be adjusted somewhat. An adjustment of plus or minus 35 percent of the focal length of the projection lens will provide for accurate imaging of the grating on the retina for 99 percent of the population.

A simplified optical schematic of the system illustrating this imaging of the grating onto the retina is provided in FIG. 7. This schematic does not include the mirror 46 and thus does not have the bend in the optic axis 50, 34. The schematic shows illumination of a single slit in the grating 44 from three points of a light source 40. Ignoring diffraction at the grating at this point, the rays of light pass through the slit and are focused onto the image 52 of the source 40.

Because the grating 44 is at the rear focal plane of lens 48 the rays of light which pass through each point of the slit in the grating form a bundle of parallel rays which pass through the image plane 52 of the light filament. Similarly, light rays which pass through any other point in the grating are focused into parallel rays by the lens 48 and pass through the image 52. These rays have the appearance of being emitted from a source at infinity and are thus properly focused onto the ocular fundus by the eye. In the present system, the stripe image on the fundus is a reduction of the grating to about 17%.

The above description is without regard to diffraction at the grating 44. Even with diffraction light rays from each point along the slit at the focal plane are focused into parallel bundles of light directed toward the eye. In fact, when a coherent beam of collimated light from a laser is used to illuminate the grating, it is diffraction that results in the diverging rays between the grating and lens 48. The rays are collimated at the lens 48 to provide an apparent image of the grating at infinity.

Figure 8A:
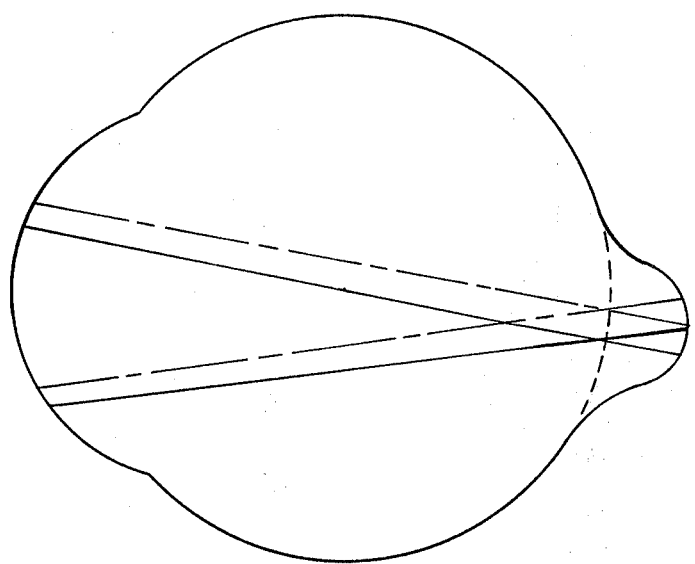
FIGS. 8A and 8B are optical schematics illustrating the depth of field limitations of the system.
Figure 8B:
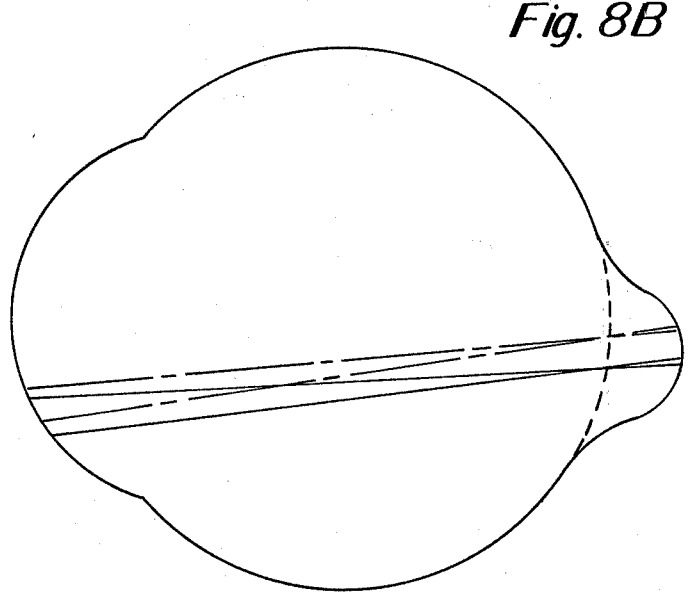

The system shown in FIG. 7, having a large filament at the light source 40 and no aperture stop other than the lenses themselves, provides a clear image of the grating on a retina having no cup at the optic disc. However, the depth of field of the image on the retina is shallow as shown in FIG. 8A. In that figure the bold lines represent the outer limits of rays forming the image of one slit. The thin lines represent the outer limits of rays forming the image of another, higher slit. As the rays from each image point diverge past the retinal surface, illustrated by broken lines, the edges of the stripes become blurred and may even overlap. This would make calculations of the depth of the cup based on bending of the lines impossible. To provide for a greater depth of field of the grating image, the present system further includes an aperture stop. In the preferred system this stop is the mirror 46. The mirror only reflects a portion of the light source image 52. Thus, as shown in FIG. 8B the rays which strike the eye are limited to a smaller surface area at the eye lens. Consequently, there is less divergence of the rays beyond the focal point along the retina and less blurring of the edges of the stripes even along the deepest portions of the optic disc cup.

The size and position of the mirror 46 are determined by several design considerations. As already noted, the mirror serves as an aperture stop. The surface area of the eye through which the wedge of light from the mirror passes is determined by both the width of the mirror and the distance of the mirror from the eye. The closer a mirror of given width is to the eye the more effective that mirror is in increasing the field of view of the system. Of course, the mirror must not be so close to the eye as to present a risk of its contacting and possibly damaging the eye. The further the mirror is from the eye the more narrow it must be to provide a given field of view. A too narrow mirror is difficult to fabricate and handle and also limits the percentage of light from the light source which actually strikes the eye. A further limitation on the mirror is that it must not obstruct the view of the fundus camera. The optic axes of the projector and camera at the eye must be parallel; and because the pupil of a patient's eye may have a diameter as small as four millimeters the system must allow for those axes to be as close as three millimeters to each other. The mirror must also be placed between the front lens of the fundus camera and the eye sufficiently far from each that the light can be projected onto the mirror without being obstructed by the camera or patient. To meet all of these considerations, the present system includes a 1.5 millimeter wide mirror whose angle makes it appear to be one millimeter wide to the patient. The mirror is positioned about five millimeters from the patient's eye.

To provide for the maximum intensity of light reflected into the eye by the mirror from a given light source, the mirror should also be positioned at about the image plane of the light source. In the present system, because the light source is positioned at the rear focal plane of the collimating lens 42, the filament image plane is at the front focal plane of projection lens 48.

To allow for a maximum distance between the optic axes 32 and 34 for an eye having a given pupil diameter, the position of the mirror along the optic axis 50 may be adjusted. By increasing the distance between the parallel axes 32 and 34, the angle at which the fundus camera views the stripes is increased. The result is greater bending of the lines in the fundus photograph and a lesser error in the depth calculations. The assembly for adjusting the mirror position is shown in FIGS. 4–6. The mirror 46 is mounted to a pin 56 which is inserted into a hole in an arm 58 (FIG. 6). After an initial adjustment to set the axes 32 and 34 in parallel, rotation of the mirror is prevented by a set screw 60.

The arm 58 extends from a beam 62 which runs parallel to the projector optic axis 50. That beam can be moved axially by a thumbwheel 64. This causes the mirror to move along the axis 50 and vary the distance between the axes 32 and 34 as discussed above.

Although the aperture stop is preferably the mirror 46 positioned close to the eye, the stop may be elsewhere in the optical system. If elsewhere, it should be imaged very close to or into the eye. With such imaging of an aperture stop the mirror may be wider. A beam splitter which reflects light into the eye from the projector yet permits light to pass from the eye through the beam splitter and into the camera would also be possible. If a laser is used as the light source, the aperture stop may be the diameter of the focused laser beam.

Figure 9:
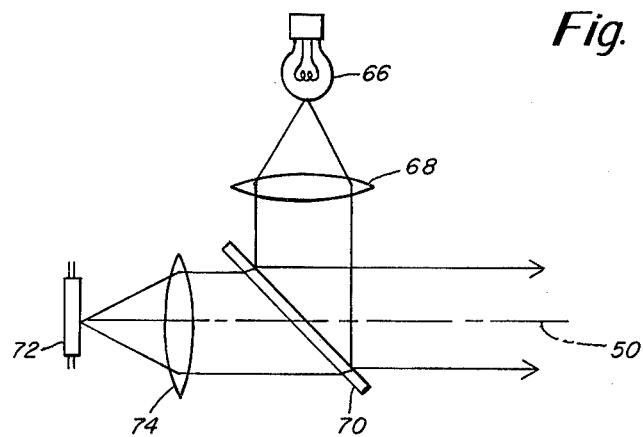
FIG. 9 is a schematic of a preferred lamp assembly to be used in the accessory.

The system thus far described includes a single light source for use both when the stripes on the ocular fundus are viewed through the camera to focus the strips and when the fundus photograph is taken. The preferred system includes an illumination arrangement such as shown in FIG. 9 which has a low intensity light source for focusing and otherwise viewing the stripes on the fundus and a high intensity flash lamp for use only when the photograph is taken. Specifically, light from a low intensity grating illuminating lamp 66 is collimated by a lens 68 and reflected by a beam splitter 70 toward the grating along the projector optic axis 50. A flash lamp 72 is positioned behind the beam splitter 70 and light from the flash lamp is collimated by a lens 74. That light is directed through the beam splitter, also along the axis 50. The flash lamp 72 is triggered by operation of the shutter button on the fundus camera through an electrical connection. Thus this system provides a high intensity flash for just the instant at which the photograph is taken but avoids the possibility of damage due to extended illumination of the eye with the high intensity lamp.

While the invention has been particularly shown and described with reference to preferred embodiments thereof, it will be understood by those skilled in the are that various changes in form and details may be made therein without departing from the spirit and scope of the invention as defined by the appended claims. For example, the stripe image may be enhanced by injecting a flourescent dye into the blood stream in accordance with the principle of flourescein angiography.

I claim:

1. In a photogrammetry system of obtaining ocular fundus contour information, the system including a camera for photographing the retina and optic disc of a naked eye along a camera optic axis through the pupil of the eye and a projector for projecting and imaging a plurality of light stripes onto the retina and optic disc of the fundus through the pupil along a projection optic axis spaced from the camera optic axis at the pupil, the projector comprising, along the projector optic axis:

- a light source;
- a projector lens system spaced from the eye;
- a grating positioned at about the rear focal plane of the projector lens system such that the grating is imaged onto the retina and optic disc of the fundus by the optical power of the projector lens system and the eye without a contact lens on the eye;
- a mirror for bringing the camera axis and projection axis into a parallel relationship at the eye, the mirror providing a grating image on the retina which spans the optic disc of the eye while permitting return light to pass to the camera to image the grating at the camera; and
- an aperture stop near or imaged near the pupil, the stop being sufficiently small to provide a depth of field corresponding to the depth of the optic disc cup and sufficiently near or imaged sufficiently near the eye to provide an image of the grating on the retina which spans the optic disc.

2. A system as claimed in claim 1 in which the aperture stop is a narrow mirror positioned near the pupil along the projector optic axis.

3. A system as claimed in claim 2 wherein the mirror is positioned about five millimeters from the pupil and is about one millimeter wide.

4. A system as claimed in claim 2 wherein the light source is positioned at about the rear focal plane of a collimating lens and the mirror is positioned at about the front focal plane of the projector lens.

5. A system as claimed in claim 1 wherein the aperture stop is an aperture positioned adjacent the light source.

6. A system as claimed in claim 1 wherein the aperture stop is formed by the light source itself.

7. A system as claimed in claim 1 wherein the light source is a laser.

8. A system as claimed in claim 1 wherein the projector is an accessory for mounting to a conventional fundus camera and which may be readily removed from the camera.

9. A system as claimed in claim 8 wherein the projector includes an optical rail fixed to a sleeve that sleeve being fitted over the front lens housing of a fundus camera.

10. A camera accessory comprising a projection lens system for projecting and imaging a plurality of light stripes onto the retina and optic disc of the eye to be photographed utilizing the eye's optics, the accessory comprising:

- a light source;
- a projection lens system;
- a grating at about the rear focal plane of the lens system such that the grating is imaged onto the retina and optic disc of the fundus by the optic power of the projection lens system and the relaxed eye;
- a narrow mirror at about the image plane of the light source for reflecting light along the projection axis into the eye and for providing an aperture stop in the projection system near the pupil of the eye; and
- means for positioning the mirror near to the eye, the mirror being sufficiently small and sufficiently close to the eye to provide a depth of field of the grating image on the retina of at least about 1 mm and to provide a grating image on the retin at least 1.5 mm wide to span the optic disc of the eye without interfering with the return light to a fundus camera.

11. An accessory as claimed in claim 10 further comprising a mirror for reflecting light from the projection lens system into the eye which is to be photographed.

12. An accessory as claimed in claim 10 or 11 further comprising a sleeve sized to surround the lens housing of a fundus camera and support the accessory from the camera.

13. A camera accessory for projecting and imaging a plurality of light stripes onto the retina and optic disc through the pupil, the accessory comprising:

- a stripe projector aligned along a projection optic axis;
- a mirror about 1.5 mm wide for reflecting the stripe projection into the eye; and
- a sleeve sized to fit over a lens housing of a camera, the sleeve providing for proper positioning of the stripe projector such that the projection axis is in a proper predetermined relationship with the camera optic axis in parallel at the eye and such that the mirror is spaced about 5 mm from the eye.

14. In a photogrammetry system for obtaining ocular fundus contour information, the system including a camera for photographing the retina and optic disc of a naked eye along a camera optic axis through the pupil of the eye, a projector for projecting and imaging a plurality of light stripes onto the retina and optic disc through the pupil along a projection optic axis spaced from the camera optic axis at the pupil, and means for positioning a patient's head such that an eye is positioned for imaging of the light stripes onto the ocular fundus and for imaging the ocular fundus onto phtoographic film in the camera, the system characterized in that the projector comprises, along the projector optic axis:

- a light source;
- a projector lens system spaced from the eye;
- a grating positioned at about the focal plane of the projector lens system such that the grating is imaged onto the retina and optic disc of the fundus by the optical power of the projector lens system and the relaxed eye;
- a narrow mirror for reflecting light along the projection axis into the eye for providing an aperture stop in the projection system near the pupil of the eye the mirror being at about the image plane of the light source and sufficiently small and sufficiently close to the eye to provide a depth of field of at least about 1 mm at the retina and to provide a grating image on the retina of at least 1.5 mm wide which spans the optic disc of the eye without interfering with the return light to a camera where the ocular pupil diameter is about 4 mm.; and
- means for fixing the projector to the front lens housing of the camera to provide a predetermined proper relationship between the projection optic axis and the camera optic axis.

15. A system as claimed in claim 14 wherein the means for fixing the projector to the lens housing is a sleeve which surrounds the front lens housing of the fundus camera.

16. The system of claim 14 in which the mirror has a width equal to or less than one-half of the minimum diameter of the pupil of the human eye.

17. The system of claim 14 in which the mirror has a width of about 1.5 millimeters and is positioned about 5 millimeters from the eye.

* * * * *